(12) United States Patent
Zhang et al.

(10) Patent No.: US 8,092,705 B2
(45) Date of Patent: Jan. 10, 2012

(54) SIMPLE METHOD FOR INTRODUCING MAGNETIC PARTICLES INTO A POLYMER

(75) Inventors: Congyun Zhang, Beijing (CN); Weidong Zhou, Beijing (CN)

(73) Assignee: Beijing Dingguochangsheng Biotech, Co. Ltd., Beijing (CN)

( * ) Notice: Subject to any disclaimer, the term of this patent is extended or adjusted under 35 U.S.C. 154(b) by 0 days.

(21) Appl. No.: 12/600,647

(22) PCT Filed: May 18, 2007

(86) PCT No.: PCT/CN2007/001622
§ 371 (c)(1),
(2), (4) Date: Feb. 1, 2010

(87) PCT Pub. No.: WO2008/141475
PCT Pub. Date: Nov. 27, 2008

(65) Prior Publication Data
US 2010/0163778 A1    Jul. 1, 2010

(51) Int. Cl.
C04B 35/26 (2006.01)
C04B 35/64 (2006.01)

(52) U.S. Cl. ............ 252/62.63; 252/62.62; 252/62.56

(58) Field of Classification Search ............ 252/62.55, 252/62.54, 62.51 R, 62.56, 62.62, 62.63, 252/62.64
See application file for complete search history.

(56) References Cited

U.S. PATENT DOCUMENTS

| | | | |
|---|---|---|---|
| 4,774,265 A | | 9/1988 | Ugelstad |
| 4,873,102 A * | | 10/1989 | Chang et al. .............. 427/130 |
| 5,283,079 A * | | 2/1994 | Wang et al. ................ 427/2.13 |
| 5,322,756 A * | | 6/1994 | Ziolo ........................ 430/114 |
| 5,670,078 A * | | 9/1997 | Ziolo ........................ 516/77 |
| 6,048,920 A | | 4/2000 | Ziolo |
| 2004/0224021 A1* | | 11/2004 | Omidian et al. ............ 424/484 |
| 2005/0175702 A1* | | 8/2005 | Muller-Schulte ............ 424/486 |
| 2006/0040388 A1* | | 2/2006 | Bromberg et al. ............ 435/375 |

FOREIGN PATENT DOCUMENTS

| | | |
|---|---|---|
| CN | 1302831 | 7/2001 |
| CN | 1541712 | 11/2004 |
| CN | 1600800 | 3/2005 |
| CN | 1712457 | 12/2005 |
| DE | 19800294 | 7/1999 |
| JP | 61060758 | 3/1986 |

* cited by examiner

*Primary Examiner* — Jerry Lorengo
*Assistant Examiner* — Lynne Edmondson
(74) *Attorney, Agent, or Firm* — Barry L. Davidson; Davis Wright Tremaine, LLP

(57) ABSTRACT

The present invention provides a simple method for introducing magnetic particles into a polymer for further preparing a magnetic polymer, the method using the capability of polymer to absorb $Fe^{3+}$ and other divalent metal ions $M^{2+}$, adding alkali immediately each time after absorbing $Fe^{3+}$ or $M^{2+}$, thereby generating hydrated oxide of the $Fe^{3+}$ and hydrated oxide of the divalent metal ions in sequence inside the polymer, and then heating, so that the hydrated oxide of the $Fe^{3+}$ and the hydrated oxide of the divalent metal ions are transformed into magnetic particles $MFexOy$, where M may be $Fe^{2+}$, $Zn^{2+}$, $Mg^{2+}$, $Cu^{2+}$, $Ca^{2+}$, $Ba^{2+}$, $Sr^{2+}$, $Ni^{2+}$, $Co^{2+}$, $Mn^{2+}$ and the like, and $x=1.0\sim2.0$; $y=3.0\sim4.0$. Compared with the prior art method, the present one is simpler, wider in application, and more operable.

10 Claims, No Drawings

SIMPLE METHOD FOR INTRODUCING MAGNETIC PARTICLES INTO A POLYMER

FIELD OF THE INVENTION

The present invention relates to a method for preparing a magnetic polymer, and in particular, relates to a simple method for preparing a magnetic polymer by introducing magnetic particles into a polymer.

BACKGROUND OF THE INVENTION

A magnetic polymer is a composite material composed of polymer and magnetic inorganic compound. Currently, most magnetic polymers in fastest development are required in a particle form and sized between nanometers and millimeters. Since magnetic polymers are capable of rapidly moving in a certain direction in an external magnetic field, they are widely applied in fields such as biochemistry, molecular biology, medical science, pharmaceutical science and chemical catalysis, etc, for example, they may act as powerful isolation and purification tools in studies on purification and isolation of nucleic acids and proteins, cell screening, immune analysis and clinical diagnosis, and may also used in targeting drugs. The magnetic polymer is not limited to spherical shape, which can be any geometric shape, and it may assume various kinds, including solid, hollow, porous, dumb bell-shaped, onion-shaped, micro capsular, flaky or other irregular shapes, etc.

A magnetic polymer mainly comprises two parts: one is the magnetic part, mainly a kind of inorganic particles, for example metal particles such as iron, cobalt and nickel, etc, or magnetic ferrite particles, for example $\gamma$-$Fe_2O_3$ and $MFe_2O_3$, where M may be Fe, Zn, Mg, Cu, Ca, Ba, Sr, Ni, Co, Mn, etc. Another part of the magnetic polymer is the polymer, and typically the magnetic particles are encapsulated inside the polymer.

Currently, the known methods for preparing a magnetic polymer are to assemble the inorganic particle part and the polymer part sequentially, which can be summarized in the following kinds.

① preparing in advance the magnetic particles and polymers, physically mixing the polymers and magnetic particles. This method is simple and less demanding, but the product is poor in shape, with wide distributions of particle diameters.

② preparing in advance the magnetic particles, and polymerizing organic monomers at the periphery of the magnetic particles. Since the inorganic particles and the organic monomers have a poor affinity, the greatest difficulty for preparing composite polymers using the organic monomer polymerization method on magnetic particles is that the monomers are hard to be polymerized at the surface of inorganic particles, but form spheres separately, which may result in vacant spheres, and the magnetic particles are unevenly distributed between spheres either. To overcome this drawback, it is necessary to process the surface of inorganic particles, but the product still can not meet the requirement.

③ preparing in advance the polymer firstly, introducing magnetic particles into the polymer. For example, U.S. Pat. No. 4,774,265 discloses a method of preparing the polymer parent substance with very even particle diameters first, and then introducing the magnetic substances into the inside of the polymer. The method requires the polymer to have functional groups capable of binding metal ions such as Fe, Co, and Ni, and only in the case where the unabsorbed ions in the solution are eliminated after absorbing sufficient divalent metal ions and $Fe^{3+}$ ions with suitable proportions, and alkaline reagents are added finally, the magnetic particles can be generated inside the polymer in situ. If a polymer has no absorption capability to the above metal ions, such polymer can not be used to prepare magnetic polymer.

The method disclosed by the U.S. Pat. No. 4,774,265 is to add a solution of a mixture of two metal ions into the polymer microsphere. This method requires the polymer microsphere to absorb divalent metal ions and $Fe^{3+}$ ions with a suitable proportion at the same time, and for oxidation-reduction reaction, the amount of the oxidization agent or reducing agent may be controlled such that the final proportion between the divalent metal ions and $Fe^{3+}$ ions is 1:2, and thereby generating magnetic $Fe_3O_4$.

However, to the polymer which has no oxidable or reducible group, use of such mixed iron salt does not have a good effect in the following aspects: firstly, it is not easy to control the absorption proportion of the divalent metal ions and $Fe^{3+}$ ions inside the polymer to be exactly 1:2; secondly, a proportion of metal irons in mixed iron salt, which is suitable for one polymer, may not be suitable for another polymer B; thirdly, it may require times of repetitive operations to obtain the magnetic transfer effect, and moreover, magnetic polymer can often not be obtained for micron or smaller polymers.

Besides, introduction of magnetic particles to carboxylic resin is disclosed in the literature "Study on Preparing Magnetic Cation Exchange Resin by Chemical Transformation Method", by Zhang Mei, Wang Busen, Zhang Yuge, He Binglin, etc, *Ion Exchange and Absorption*, 1995, 11 (4), 302-308, wherein in case the mol ratio between two iron salts being 2:1, or even 1:1, it is unable to introduce magnetic particles into the polymer, which can only be successful under the mol ratio being 1:5-1:50, and the polymer can only exhibit a strong magnetism after repeating the introduction three times or more. It is speculated that weak acid type ion exchange resin has a clear selectivity, which has a strong absorption capability to $Fe^{3+}$, but weak to absorb $Fe^{2+}$, thus it needs a greatly excessive amount of $Fe^{2+}$ salt in the mixed iron salt. Besides, when magnetic transferring, the increase of magnetism is not proportional, and there may have more complex affecting factors besides the selectivity.

Besides, the information as disclosed in Example 2 of the U.S. Pat. No. 4,783,102 also shows a similar situation, wherein when using a 1:1 iron salt mixture solution, a sulfonated cross-linked polystyrene ion-exchange resin having a strongly acidity only has a slight magnetism after the first magnetism transformation, and only exhibits an apparent magnetism after times of magnetism transformation.

Thus, a method which is simpler, wider in application and more operable is needed.

SUMMARY OF THE INVENTION

An object of the present invention is to provide a simple method for preparing a magnetic polymer by introducing magnetic particles into the polymer.

The method according to the present invention comprises steps of:

1) putting a polymer in a container, the polymer having groups capable of absorbing $Fe^{3+}$ ions and $Fe^{2+}$ ions or other divalent metal ions, and having large pores within the molecule or being capable of forming a microporous gel in a solution;

2) adding a $Fe^{3+}$ salt solution into the polymer of 1), and stirring to make the polymer absorb $Fe^{3+}$ ions;

3) washing the resultant to eliminate unabsorbed $Fe^{3+}$ ions, and then adding an alkaline solution to control the pH value in a range from 9 to 14, stirring, and then washing to neutral;

4) adding a divalent metal salt solution into the polymer of 3), stirring to make the polymer absorb divalent metal ions;

5) washing the resultant to eliminate the unabsorbed divalent metal ions;

6) introducing an inert gas, adding an alkaline solution to control the pH value in a range from 9 to 14, stirring and heating, maintaining for a period of time, and thus the magnetic polymer is produced.

In step 1) of the method of the present invention, the polymer is a wet cross-linked polymer with water content weight being 0.1~100 times.

In step 1) of the method of the present invention, the polymer is a water-soluble natural polymer and derivatives thereof, including pectine, heparin, animal serum albumin, gelose, glucan and their derivatives.

In step 1) of the method of the present invention, the polymer is a synthetic polymer having cation exchange capability, the synthetic polymer is formed by homopolymerization or copolymerization of monomers having groups such as —$SO_3H$ (sulfonic group), —COOH (carboxyl group), —$PO_3H_2$ (phosphate group), —CONH—OH (hydroximic acid group) in the molecule; or a polymer introduced with the above groups by chemical modification.

In step 1) of the method of the present invention, the polymer is a synthetic polymer having single coordination or chelation capability, including polyacrylamide, polyvinyl alcohols, polyvinyl pyridine, polyvinyl amine, or imine carboxylic acids bearing both amino group and carboxyl group in a molecule (—$NHCH_2COOH$, —$N(CH_2COOH)_2$, etc), phosphoramidic acid structure (—$NHCH_2PO_3H_2$), proline structure

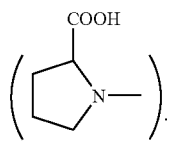

In step 2) of the method of the present invention, the $Fe^{3+}$ salt includes $FeCl_3$ and its hydrates, $Fe(NO_3)_3$ and its hydrates, $(NH_4)Fe(SO_4)_2$ and its hydrates, $(NH_4)_3[Fe(C_2O_4)_3]$ and its hydrates, $Fe(ClO_4)_3 \cdot xH_2O$, ferric citrate, and ferric ammonium citrate.

In step 3) and step 6) of the method of the present invention, the alkaline solution includes any one of KOH, NaOH, and ammonia.

In step 4) of the method of the present invention, the divalent metal salt is a divalent metal compound which is capable of forming magnetic $MFe_xO_y$ particles with $Fe^{3+}$ ions, wherein M includes $Fe^{2+}$, $Zn^{2+}$, $Mg^{2+}$, $Cu^{2+}$, $Ca^{2+}$, $Ba^{2+}$, $Sr^{2+}$, $Ni^{2+}$, $Co^{2+}$, $Mn^{2+}$; $x=1.0~2.0$; and $y=3.0~4.0$.

In step 4) of the method of the present invention, the divalent metal salt includes $FeCl_2$ and its hydrates, ferrous oxalate, $(NH_4)_2Fe(SO_4)_2$ and its hydrates, $FeSO_4$ and its hydrates, $MgCl_2$ and its hydrates, $MnSO_4$ and its hydrates, $CoCl_2$ and its hydrates, $NiCl_2$ and its hydrates.

In step 3) and step 6) of the method of the present invention, the alkaline solution includes any one of KOH, NaOH, and ammonia.

The method provided by the present invention needs no consideration of the absorption proportion of $M^{2+}/Fe^{3+}$ inside the polymer, and after separately adding $Fe^{3+}$ and $M^{2+}$, a magnetic polymer can be obtained by only performing magnetism transformation for one time. The method of the present invention is particularly advantageous to small sized polymers for example in nanometers or micros.

DESCRIPTION OF THE PREFERRED EMBODIMENTS

The method of the present invention is to introduce magnetic particles into a shaped polymer, by utilizing the capability of the polymer to absorb $Fe^{3+}$ ions and other divalent metal ions $M^{2+}$, the method comprises: adding $Fe^{3+}$ ions and divalent metal ions in sequence, adding alkaline immediately after each time of absorbing a cation, thereby generating hydrated oxide of the $Fe^{3+}$ ions and hydrated oxide of divalent metal ions inside the polymer in sequence; and then heating, so that the hydrated oxide of the $Fe^{3+}$ ions and hydrated oxide of divalent metal ions are transformed into magnetic particles $MFe_xO_y$, M may be $Fe^{2+}$, $Zn^{2+}$, $Mg^{2+}$, $Cu^{2+}$, $Ca^{2+}$, $Ba^{2+}$, $Sr^{2+}$, $Ni^{2+}$, $Co^{2+}$, $Mn^{2+}$, and etc, wherein $x=1.0~2.0$; $y=3.0~4.0$.

The polymer applicable to the present invention is firstly a cross-linked water soluble polymer or a strongly hydrophilic polymer. If the polymer have a weak hydrophility, the ions are hard to be dispersed into the inside of the polymer, and the polymer absorbs very small amount of ions or the absorption balance time is unduly long, which causes the amount of magnetic particles inside very small, and the preparation step is too complex to have a practical value. The water soluble polymer is preferably subjected to a cross-linking processing, including physical cross linking and chemical cross linking. For example, gelose can be dissolved in water at a high temperature, while it can only be swelled, not dissolved, in water at room temperature, which is a typical example for physical cross linking. What is used most is chemical cross linking, and the reason for preferably using chemical cross linking is that it is not affected by a general solvent and temperature changes or other conditions, thus can ensure the material's morphological stability. It is true that cross linking will affect the hydrophility of a polymer. It has been found that some water soluble polymers may lose water absorption capability after high level of cross linking, but it is easy to maintain the balance between good hydrophility and mechanical strength of a polymer by adjusting the level of cross linking.

There are many kinds of water soluble polymers, or there have been many simple methods to modify polymers to enhance their hydrophility, and a polymer having many strongly hydrophilic groups will also have strong absorption capability to $M^{2+}/Fe^{3+}$. The strongly hydrophilic groups are mostly polar groups, which always have a strong absorption capability to metal ions by coordination or forming ionic bonds.

The water soluble polymer or strongly hydrophilic polymer in the present invention may be conveniently improved in the hydrophility by polymerizing water soluble monomers carried with strongly hydrophilic groups by themselves or introducing strongly hydrophilic groups into the polymer. Examples of chemical groups with strong hydrophility and strong absorption capability to $M^{2+}/Fe^{3+}$ are, for example, —$SO_3H$ (sulfonyl group), —OH (alcoholic hydroxyl group, phenolic hydroxyl group), —O— (ether, epoxy group), —$CONR_2$ (acylamino group, R=H or alkyl), —$NH_2$ (primary amine),

(secondary amine),

(tertiary amine),

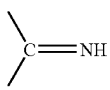

(imine),

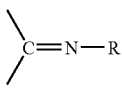

(schiff base),

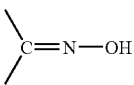

(oxime),
—$AsO_3H_2$ (arsenic acid group), —$SeO_3H_2$ (selenic acid group), —$SO_2H$ (sulfinic acid group), —COOH (carboxyl group), —COOR (carboxylate group), —CONH—OH (hydroximic acid group), —CN (cyano group), —$CONHNH_2$ (hydrazide), —N=O (nitrogen oxide),

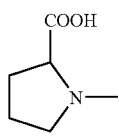

(proline),
—CO— (aldehyde, ketone, quinone), —PHO(OH), —PHO$(OH)_2$, —PO$(OH)_2$, —$NO_2$ (nitro group), —NO (nitroso group), —NHOCO— (carbamate group), —NHCO—NH— (ureido group), nitrogen-containing heterocyclic ring, —SH (thiol, thiophenol), —S— (thioether), —S=O (sulphone and sulphoxide),

(sulfaldehyde, thioketone),
—COSH (thiocarboxylic acid), —CSSH (carbodithioic acid), —CS—S—S—CS—, —$CSNH_2$ (thioacid amide), —SCN (sulfocyanate),

(mono-, di-, or tri-alkyl or aryl phosphine, etc),
amino carboxylic acid series, —$NHCH_2PO(OH)_2$ phosphoramidic acid series, $H(NHCH_2CH_2)_nNH_2$ (polyethylene polyamine series), —N=N— (azo), etc.

Examples of the water soluble polymer with strong hydrophility and bearing a chemical group having a strong absorption capability to $M^{2+}/Fe^{3+}$ or strongly hydrophilic polymer are as follows: (1) water soluble natural polymers such as modified starch, modified cellulose, pectine, heparin, some proteins (soybean protein, fibroin, gluten), animal serum albumin, gelose, chitosan, glucan, alginic acid and their derivatives; (2) polymers which dissociates completely or partially cations in an aqueous solution, such as poly(meth)acrylate, polyglutamic acid, hydrolysate of copolymer of polyacrylate and vinyl acetate, copolymer of acrylic acid and acrylamide, polyvinylsulfonate, polystyrene sulfonate, polymaleic anhydride, polymethyl methacrylate-vinyl acetate pressurized hydrolyzate, polyacrylonitrile hydrolyzate, wherein the strong acid type has sulfonic group, with ethylene, styrene or meltbond ureaformaldehyde polycondensation system as the backbone; the weak acid type typically has carboxylic acid or phosphorous acid group. (3) hydrophilic polymers which are capable of forming simple coordination with $M^{2+}/Fe^{3+}$, such as polyacrylamide, polyvinyl alcohol, poly alkane oxide, polyoxyethylene, polyvinyl imine, polyvinyl pyridine, and polyvinyl amine; (4) polymers having more than two coordination sites and thereby chelation capability, for example, EDTA type resin with cross-linked styrene as the backbone and introducing imine polycarboxylic acid, which may also be obtained by polymerization from olefine monomers with imine carboxylic acid, such resin has a strong absorption capability to most $M^{2+}$ and $Fe^{3+}$, typical imine (poly)carboxylic acid chelating groups are: imine diacetic acid, imine acetic acid propionic acid, nitrilotriacetic acid, N-(2-hydroxyethyl)ethylenediamine-triacetic acid, ethylene diamine tetraacetic acid, diethylene triamine pentaacetic acid, ethylene diamine-N,N'-diacetic acid type resin produced by reaction between polyethylene imine and chloroactic acid; with polyvinyl alcohol as the framework, introducing imine carboxylic acid group by reacting with epoxy-bearing amidodiacetate, chelating resin with β-diketone structure obtained by polymerizing methyl acroloyl acetone monoers; β-ketoacid ester generated by grating reaction between polyvinyl alcohol and ketene; a chelate with

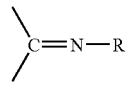

structure formed by condensation reaction of polyvinyl amine as the backbone with salicylaldehyde derivatives; a chelating resin with cross-linked styrene as the backbone and introducing phosphoramidic acid on the benzene ring, or a chiral chelating resin with cross-linked polyvinyl alcohol as the backbone and introducing L-proline

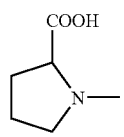

after activation by chloroepoxy propane.

$Fe^{3+}$ ions and other divalent metal ions are absorbed to the polymer via coordination bond/ion bond. The coordination bond/ion bond formed between the absorption groups on the polymer and the metal ions are reversible. After adding alkali, for example, sodium hydroxide, the coordination groups or ions on the polymers will resume their original forms, and then the metal ions are exchanged by $Na^+$ ions and the like, thereby forming a hydrated oxide and being deposited in the polymers. For example, firstly a kind of metal ion, for example $Fe^{3+}$, is absorbed and after adding alkali, transformed into the hydrated oxide; then another kind of divalent metal iron, for example $Fe^{2+}$, is absorbed and also transformed into the hydrated oxide by adding alkali; and once heating again, the two hydrated oxides generate magnetic particles $MFe_xO_y$, where M may be $Fe^{2+}$, $Zn^{2+}$, $Mg^{2+}$, $Cu^{2+}$, $Ca^{2+}$, $Ba^{2+}$, $Sr^{2+}$, $Ni^{2+}$, $Co^{2+}$, $Mn^{2+}$ and the like, wherein $x=1.0\sim2.0$; $y=3.0\sim4.0$. By using the method of the present invention, it typically needs only magnetism transformation once to obtain strong magnetism satisfying the use requirements, and if higher magnetism content is required, repeated reactions are allowed. Besides, according to the present invention, two kinds of ions are absorbed respectively in sequential two steps, the advantage of which is that the absorption of any kind of ion is not affected by other ions, which needs no consideration of interaction between two kinds of ions at all; further the method is applicable to polymers with large particle diameters or small large diameters, and it is not subject to the influence of microcosmic environment.

The magnetic polymers prepared according to the method of the present invention are widely applicable in fields such as catalytic study, magnetic recording materials, magnetic resonance image, painting, cosmetics and chemical catalysis. The magnetic polymer microspheres are also widely applicable in fields such as cell biology, molecular biology, immunology, medical science and pharmacology, for example by binding antibodies to magnetic polymer microspheres, cancer cells can be isolated from an organism, thus the magnetic polymer microspheres are a powerful tool for isolation and purification. Magnetic polymers can also be used for thermal therapy of tumor, which is a promising therapy for tumor treatment, where the treatment purpose is achieved by heating effect of magnetic polymers distributed in the tumor tissues upon applying an external alternating magnetic field. Or by forming a targeting drug by loading anticancer drugs on the magnetic polymers, the anticancer drugs, under the guide of magnetic field, are enriched in the focus part, thereby reducing noxious side effects of the drugs on the normal cells.

EXAMPLES

Hereinafter, the present invention is further described with reference to the examples, but the purpose of these examples is not for limiting the protection scope of the present invention.

Example 1

1 g of millimeter micropore type acrylic cation exchange resin 110 (produced by the Chemical Plant of NanKai University), in hygrometric state, water content being 52~62%, particle diameter being 0.315~1.25 mm, was weighted.

10 ml of 0.1 mol/L $FeCl_3 \cdot 6H_2O$ solution were added and stirred, and then deionized water was used to wash out unabsorbed $Fe^{3+}$. Concentrated ammonia was added to make the pH to 10, and the resultant was stirred, and then washed with deionized water to neutral. 10 ml of 0.1 mol/L $(NH_4)_2Fe(SO_4)_2 \cdot 6H_2O$ solution were added to the former polymer, stirred, and then washed with deionized water to remove unabsorbed $Fe^{2+}$. Concentrated ammonia was added to make the pH to 10 under the protection of nitrogen gas, and the resultant was stirred and heated to 80° C. to react for 30 minutes, thereby obtaining magnetic polymer 1, with a saturated magnetization strength of 21.02 emu/g.

Example 2

Using 1 g of millimeter macropore type acrylic cation exchange resin D151 (produced by the Chemical Plant of NanKai University), in hygrometric state, water content being 60~72%, particle diameter being 0.315~1.25 mm, magnetic polymer 2 was prepared according to the method of example 1, except for changing the heating temperature to be 70° C. for reacting for 60 minutes. The measured saturated magnetization strength of the magnetic polymer 2 was 35.70 emu/g.

Example 3

Using 1 g of millimeter macropore type sulfonic group-bound styrene cation exchange resin D72 (produced by the Chemical Plant of NanKai University), in hygrometric state, water content being 50~55%, particle diameter being 0.315~1.25 mm, magnetic polymer 3 was prepared according to the method of example 1, except for controlling the pH value at 14, heating to 90° C. for reacting for 20 minutes. The measured saturated magnetization strength of the magnetic polymer 3 was 28.04 emu/g.

Example 4

Using 1 g of millimeter macropore type phosphate group-bound styrene cation exchange resin DLT (produced by the Chemical Plant of NanKai University), in hygrometric state, water content being 55~65%, particle diameter being 0.315~1.25 mm, magnetic polymer 4 was prepared according to the method of example 1, except for controlling the pH value at 12, heating to 80° C. for reacting for 60 minutes. The measured saturated magnetization strength of the magnetic polymer 4 was 31.55 emu/g.

As seen from examples 1, 2, 3 and 4, magnetic particles may be smoothly introduced into a polymer having cation exchange capability through magnetism transformation for once by using the method of the present invention.

Example 5

Using 1 g of millimeter macropore type imine carboxylic acid-bound styrene chelating resin D401 (produced by the Chemical Plant of NanKai University), in hygrometric state, water content being 45~55%, particle diameter being 0.315~1.25 mm, magnetic polymer 5 was prepared according to the method of example 1, except for controlling the pH value at 12, heating to 80° C. for reacting for 30 minutes. The measured saturated magnetization strength of the magnetic polymer 5 was 23.91 emu/g.

Example 6

A millimeter micropore type imine carboxylic acid-bound styrene chelating resin was synthetic by a method comprising: dissolving 2.3 g of polyvinyl pyrrolidone (PVP K-30) in 180 ml ethanol and 20 ml DMSO, and transferring into a polymerization bottle; and then adding 9.8 ml p-chloromethylstyrene (containing 0.2 ml divinylbenzene) dissolved with 200 mg azobisisobutyronitrile (AIBN); introducing nitrogen gas for 15 minutes; sealing the polymerization bottle, putting into 70° C. oil bath, stirring at a speed of 120 rotations/minute, and reacting for 24 hours; cooling to room temperature, centrifuging, washing 4 times by ethanol, and drying; adding 8 g of the above spherical p-chloromethylstyrene-divinylbenzene copolymer into 38 g dichloroethane, cooling to 5-10° C., and then adding 1.36 g dimethyl aminoethanol, stirring the mixture at a temperature lower than 10° C. for reacting for 1 hour, and then heating and refluxing for 1 hour; after cooling, centrifuging and isolating, sufficiently washing with methanol, and adding the partially quaternized microspheres to 18.5 g methanol, heating with 37.3 g aqueous solution containing 22.7 g sodium imine diacetate for reaction, refluxing and stirring for reaction for 4 hours, and then cooling, centrifuging and isolating the resultant.

Using 1 g of the above prepared millimeter micropore type imine carboxylic acid-bound styrene chelating resin, particle diameter being 1.25 μm, in hygrometric state, water content being 30~40%, magnetic polymer 6 was prepared according to the method of example 1, except for controlling the pH value at 12, heating to 80° C. for reacting for 60 minutes. The measured saturated magnetization strength of the magnetic polymer 6 was 25.37 emu/g.

Example 7

A millimeter micropore type β-diketone (—CO—$CH_2$—CO—) structure-bound chelating resin was synthetic by a method comprising: taking 30 ml distilled water, adding 0.5 g polyvinyl alcohol (PVA) and 4.5 g NaCl, after dissolution, adding 5 drops of 0.1% methylene blue; taking 5 g methyl acryloyl acetone, 0.25 g divinylbenzene, 52.5 mg BPO, which, after dissolution, are added into the aqueous phase; controlling the stirring speed, heating to 50° C. for 4 hours, 65° C. for 4 hours, and 80° C. for 12 hours; cooling after the reaction ends, washing by hot water, then washing by ethanol, and drying. The prepared polymer having β-diketone (—CO—$CH_2$—CO—) structure had a particle diameter of 0.315~1.25 mm, in hydrometric state with water content 20~40%.

Using 1 g of the above prepared millimeter micropore type β-diketone (—CO—$CH_2$—CO—) structure-bound chelating resin, magnetic polymer 7 was prepared according to the method of example 1, except for controlling the pH value at 12, heating to 80° C. for reacting for 30 minutes. The measured saturated magnetization strength of the magnetic polymer 7 was 30.66 emu/g.

As seen from Examples 5, 6 and 7, for a synthetic polymer with single coordination or chelating capability and its derivatives, magnetic particles can be smoothly introduced through magnetic transformation for once by the method of the present invention.

Example 8

A micron macroporous monodisperse polyacrylic acid cross-linked microsphere was synthetic by a method comprising:

(1) taking 20 mg polymethyl methacrylate prepared by dispersion polymerization with a diameter of 2.69 μm, dispersed in 2.5 ml aqueous solution (the aqueous solution containing 0.1% sodium lauryl sulfate, 0.25% polyvinyl alcohol); taking 3 g organic matter (1.5 g toluene, 1.3 g methyl acrylate, 0.2 g divinyl benzene, and 60 mg benzoyl peroxide) to be dispersed in 15 ml dispersion liquid (an aqueous solution containing 0.25% sodium lauryl sulfate, 0.6% polyvinyl alcohol), and adding 20 mg NaCl; ultrasonic dispersing for 30 minutes, and then putting the emulsion once-for-all into a seed dispersion liquid, and swelling for 24 hours at the room temperature.

(2) polymerizing, adding 5 drops of 0.1% aqueous methylene blue solution, heating to 70° C. for polymerization reaction for 24 hours.

(3) washing, centrifuging, and then washing with hot distilled water by dispersing/centrifuging for 4 times, and washing with acetone by dispersing/centrifuging for 4 times.

(4) hydrolyzing the resultant of (3): taking 1 g carboxylic ester polymer microsphere, adding 10 ml ethanol for immersion for 30 minutes, decanting the ethanol, and then directly adding into 20 ml of 20% aqueous NaOH solution, stirring for 6 hours at 80° C., washing by deionize water to neutral, obtaining the macroporous monodisperse polyacrylic acid cross-linked microsphere, particle diameter 4.73 μm, in hydrometric state with water content 140~160%.

Using 1 g of the above prepared micron macroporous monodisperse polyacrylic acid cross-linked microsphere, magnetic polymer 8 was prepared according to the method of example 1, except for controlling the pH value at 13, heating to 80° C. for reacting for 30 minutes. The measured saturated magnetization strength of the magnetic polymer 8 was 35.17 emu/g.

Example 9

A submicron microporous monodisperse polyacrylic acid cross-linked microsphere was synthetic by a method comprising: adding in sequence in a 500 ml glass polymerization reactor disposed in a water bath tank 100 ml double distilled water, 7.498 g methyl acrylate, and 0.872 g divinyl benzene, starting to stir, introducing nitrogen gas and exhausting oxygen; about 20 minutes later, adding 6.4 mg potassium persulphate and heating to 60° C., after 24-hour reaction, terminating the reaction; flocculating with saturated aqueous NaCl solution, centrifuging, and washing by ethanol; adding the above polymer into 10 ml ethanol for immersion for 30 minutes, decanting the ethanol, and then directly adding into 20 ml of 20% aqueous NaOH solution, stirring for 6 hours at 80° C., washing by deionize water to neutral, obtaining the microporous monodisperse polyacrylic acid cross-linked microsphere, particle diameter 613 nm, in hydrometric state with water content ~120%.

Using 1 g of the above prepared submicron microporous monodisperse polyacrylic acid cross-linked microsphere, magnetic polymer 9 was prepared according to the method of example 1, except for controlling the pH value at 12, heating to 80° C. for reacting for 30 minutes. The measured saturated magnetization strength of the magnetic polymer 9 was 21.85 emu/g.

As seen from examples 8 and 9, for a synthetic polymer with even particle diameter and having cation exchange capability, magnetic particles may be smoothly introduced through magnetism transformation for once by using the method of the present invention.

Example 10

A cross-linked polyvinyl pyrrolidon powder was synthetic by a method comprising: adding 2 g N-vinyl pyrrolidon, 0.02 g N,N'-methylenebisacrylamide, 0.02 mg AIBN, 10 ml solvent (an aqueous solution containing 5% sodium sulfate and 5% disodium hydrogen phosphate) into a three-necked flask, introducing nitrogen gas for 10 minutes, and then stirring and refluxing at 70° C. for reaction for 80 minutes, washing clean the resultant by distilled water, sufficiently drying and pulverizing at 120° C., thereby obtaining amorphous solid powder of the cross-linked polyvinyl pyrrolidon.

Using 1 g of the above prepared amorphous solid powder of the cross-linked polyvinyl pyrrolidon, in hydrometric state with water content ~220%, magnetic polymer 10 was prepared according to the method of example 1, except for controlling the pH value at 12, heating to 80° C. for reacting for 30 minutes. The measured saturated magnetization strength of the magnetic polymer 10 was 25.39 emu/g.

Example 11

Irregular shaped γ-polyglutamic acid polymer was synthetic by the following method. γ-polyglutamic acid with a weight average molecular weight of 500,000 prepared by fermenting *Bacillus subtilis* was used as a raw material. Into 100 ml distilled water, 12 g γ-polyglutamic acid were added and sufficiently and uniformly dissolved, then 6 g glycol diglycidyl ether were added. The resultant was stirred to be uniform, and reacted under vibration in a water bath at constant 60° C. for 48 hours. The product was washed by ethanol, water, and again ethanol, and dried, thereby obtaining the irregular shaped polyglutamic acid cross-linked product.

Using 1 g of newly synthetic irregular shaped γ-polyglutamic acid polymer, in hydrometric state with water content ~300%, magnetic polymer 11 was prepared according to the method of example 1, except for controlling the pH value at 12, heating to 80° C. for reacting for 30 minutes. The measured saturated magnetization strength of the magnetic polymer 11 is 22.94 emu/g.

As seen from Examples 10 and 11, for an irregular shaped synthetic polymer with single coordination or chelating capability, magnetic particles can be smoothly introduced through magnetic transformation for once by the method of the present invention.

Example 12

A high water-content millimeter micropore type polyacrylic acid cross-linked microsphere was synthetic by a method comprising: taking 30 ml distilled water, adding 0.5 g PVA and 4.5 g NaCl, after dissolution, adding 5 drops of 0.1% methylene blue; taking 5 g methyl acrylate, 0.25 g EGDMA, 52.5 mg BPO, which, after dissolution, are added into the aqueous phase, controlling the stirring speed, heating to 50° C. for 4 hours, 65° C. for 4 hours, and 80° C. for 12 hours; cooling after the reaction ends, washing by hot water, then washing by ethanol, and drying; adding into 10 ml ethanol for immersion for 30 minutes, decanting the ethanol, and then directly adding into 20 ml of 20% aqueous NaOH solution, stirring for 6 hours at 80° C., washing by deionize water to neutral.

Using 1 g of the above prepared millimeter micropore type polyacrylic acid cross-linked microsphere, in hydrometric state with water content ~500%, magnetic polymer 12 was prepared according to the method of example 1, except for controlling the pH value at 12, heating to 80° C. for reacting for 30 minutes. The measured saturated magnetization strength of the magnetic polymer 12 was 25.39 emu/g.

Example 13

A high water-content micron microporous monodisperse polymethacrylic acid cross-linked microsphere was synthetic by a method comprising: adding 1.5 g PVP K-30, 21.475 g methanol, 25 mg AIBN, 2.5 g methyl methacrylate, 50 mg ethylene glycol dimethacrylate into a glass bottle, putting a stir bar therein, controlling the stirring speed for maintaining a very stable stirring during the reaction period, and reacting for 48 hours at 55° C.; after the reaction ends, using methanol to wash repeatedly for four times, thereby obtaining polymethyl methacrylate-ethylene glycol dimethacrylate cross-linked microsphere after drying; taking 1 g of the above polymer, adding 20 ml solution of 10% KOH in ethylene glycol, refluxing for 12 hours at 175° C.~176° C., pouring into 500 ml distilled water, centrifuging, washing by deionize water to neutral.

Using 1 g of the above prepared micron micropore type monodisperse polymethacrylic acid cross-linked microsphere, in hydrometric state with water content ~310%, magnetic polymer 13 was prepared according to the method of example 1, except for controlling the pH value at 12, heating to 80° C. for reacting for 30 minutes. The measured saturated magnetization strength of the magnetic polymer 13 was 25.39 emu/g.

As seen from Example 12 and Example 13, for a high water-content polymer, magnetic particles can be smoothly introduced through magnetic transformation for once by the method of the present invention.

Example 14

A millimeter macroporous poly(2-hydroxyethyl methacrylate) cross-linked microsphere was synthetic by a method comprising: putting 100 ml aqueous solution containing 1% by mass gelatin and 15% by mass NaCl into a four-mouth bottle equipped with a stirrer, a vent tubing, a ball condensation tube, and a thermometer, adding 10 g 2-hydroxyethyl methacrylate, 2 g ethylene glycol dimethacrylate and a pore-forming agent (a mixture of 6 g ethyl acetate and 6 g lauryl alcohol); using 120 mg AIBN as the initiator, performing aqueous phase suspension polymerization under the protection of $N_2$, reacting at 65° C. for 4 hours, and 75° C. for 4 hours, thereby obtaining a white opaque bead body; filtering, washing with water, ethanol extracting, airing, and vacuum drying to a constant weight for future use.

Using 1 g of the above prepared millimeter macroporous poly(2-hydroxyethyl methacrylate) cross-linked microsphere, in hydrometric state with water content 40~50%, magnetic polymer 14 was prepared according to the method of example 1, except for controlling the pH value at 12, heating to 80° C. for reacting for 30 minutes. The measured saturated magnetization strength of the magnetic polymer 14 was 30.28 emu/g.

As seen from Example 14, for a synthetic polymer having coordination capability and obtained by polymerizing of water soluble monomers, magnetic particles can be smoothly introduced through magnetic transformation for once by the method of the present invention.

Example 15

Irregular shaped cross-linked heparin was synthetic by a method comprising: dispersing 60 g heparin into 500 g ethyl ether, adding 510 g lithium aluminium hydride, heating and refluxing for 30 minutes; neutralizing after adding water, and then filtering, drying, and thereby obtaining partially reduced heparin; dispersing the partially reduced heparin and 5 g sodium hydroxide into a mixture solution of 500 g isopropyl alcohol and 10 g water, adding 12.5 g sodium chloroacetate, reacting for 1 hour at 20° C., and then heating to 80° C. for reacting for 1 hour; filtering, neutralizing, washing, and drying the resultant, and then adding 0.5 g chloroepoxy propane, cross-linking, washing, and drying.

Using 1 g of the above prepared irregular shaped cross-linked heparin, in hydrometric state with water content ~200%, magnetic polymer 15 was prepared according to the method of example 1, except for controlling the pH value at 12, heating to 80° C. for reacting for 30 minutes. The measured saturated magnetization strength of the magnetic polymer 15 was 21.09 emu/g.

Example 16

Irregular shaped cross-linked pectine was synthetic by a method comprising: dispersing 50 g pectine into 500 g ethyl ether, adding 10.1 g lithium aluminium hydride, heating and refluxing for 30 minutes; neutralizing after adding 10 g water, and then filtering, drying, and thereby obtaining partially reduced pectine; dispersing the partially reduced pectine and 5 g sodium hydroxide into a mixture solution of 500 g isopropyl alcohol and 500 g water, adding 12.5 g sodium chloroacetate, reacting for 1 hour at 20° C., and then heating to 80° C. for reacting for 1 hour; filtering, neutralizing, washing, and drying the resultant, and then adding 0.5 g chloroepoxy propane, cross-linking, washing, and drying.

Using 1 g of the above prepared irregular shaped cross-linked pectine, in hydrometric state with water content ~200%, magnetic polymer 16 was prepared according to the method of example 1, except for controlling the pH value at 12, heating to 80° C. for reacting for 30 minutes. The measured saturated magnetization strength of the magnetic polymer 16 was 27.90 emu/g.

As seen from Example 15 and Example 16, for a water soluble natural polymer having coordination capability, magnetic particles can be smoothly introduced through once magnetic transformation by the method of the present invention.

Example 17

A millimeter macroporous type cross-linked polyvinyl alcohol microsphere was synthetic according to the method described in XU Lizhong, et al, "Synthesis of Anion Exchanger with Cross-Linked Polyvinyl Alcohol As the Carrier and Performance Study", College Chemical Journal, 1996, 17 (1), 151-155, and XU Lizhong, et al, "Synthesis of Macroporous Vinyl Acetate-Triallyl Isocyanurate Copolymer Bead Body and Structural Characterization", Functional Polymer Journal, 1996, 9 (2), 183.

Using 1 g of the above prepared millimeter macroporous type cross-linked polyvinyl alcohol microsphere, the cross-linked degree being 25%, the particle diameters ranging between 45 μm and 125 μm, OH content being 5.10 mmol/g, epoxy group content being 300 μmmol/g, in hydrometric state with water content ~110%, magnetic polymer 17 was prepared according to the method of example 1, except for controlling the pH value at 12, heating to 80° C. for reacting for 30 minutes. The measured saturated magnetization strength of the magnetic polymer 17 was 20.37 emu/g.

Example 18

L-proline-bound millimeter macroporous type cross-linked polyvinyl alcohol microsphere was synthetic based on XU Lizhong, et al, "Synthesis of Anion Exchanger with Cross-Linked Polyvinyl Alcohol As the Carrier and Performance Study", College Chemical Journal, 1996, 17 (1), 151-155, and XU Lizhong, et al, "Synthesis of Macroporous Vinyl Acetate-Triallyl Isocyanurate Copolymer Bead Body and Structural Characterization", Functional Polymer Journal, 1996, 9 (2), 183, but using L-proline to replace ethylene diamine.

Using 1 g of L-proline millimeter macroporous type cross-linked polyvinyl alcohol microsphere. with a cross-linked degree being 25%, particle diameters ranging between 45 μm and 125 μm, in hydrometric state with water content ~110%, magnetic polymer 18 was prepared according to the method of example 1, except for controlling the pH value at 12, heating to 80° C. for reacting for 30 minutes. The measured saturated magnetization strength of the magnetic polymer 18 was 28.93 emu/g.

Example 19

A millimeter macroporous type cross-linked polyvinyl amine microsphere was synthetic by a method comprising: taking a certain amount of cross-linked polyacrylamide (PAAM) in a three-necked flask, swelling with small amount of water, cooling in a cryohydrate bath, and adding 1.5 mol/L alkaline sodium hypochlorite solution at about −5° C.; when the temperature drops to about −10° C., adding 10 mol/L sodium hydroxide solution, speedily stirring, reacting for 2 hours at −10° C.~−15° C., and then reacting for 15 hours in an ice bath; pouring the reaction liquid into a great amount of ethanol, thereby obtaining a white solid matter.

Using 1 g of the above prepared macroporous type cross-linked polyvinyl amine microsphere, with a cross-linked degree being 25%, particle diameters ranging between 45 μm and 125 μm, in hydrometric state with water content ~150%, magnetic polymer 19 was prepared according to the method of example 1, except for controlling the pH value at 12, heating to 80° C. for reacting for 30 minutes. The measured saturated magnetization strength of the magnetic polymer 19 was 25.45 emu/g.

Example 20

Using 1 g of glucan cross-linked microsphere, Sephadex G-10 (produced by Pharmacia), in dry state, the particle diameter ranging between 40 μm and 120 μm, and in hydrometric state with water content ~50%, magnetic polymer 20 was prepared according to the method of example 1, except for controlling the pH value at 12, heating to 80° C. for reacting for 30 minutes. The measured saturated magnetization strength of the magnetic polymer 20 was 23.63 emu/g.

As seen example 17, example 18, example 19 and example 20, for a polymer having coordination capability, magnetic particles may be smoothly introduced through once magnetism transformation by using the method of the present invention.

Example 21

An albumen-bound glucan cross-linked microsphere was synthetic by a method comprising: taking 0.75 g Sephadex, G-75 purchased from Pharmacia in to a cuvette, adding 10 ml distilled water for swelling for several hours, changing water for three times during this swelling period; centrifuging by 150×g for 3 minutes, discarding the supernatant, retaining the swelled Sephadex about 1 ml; adding 2 ml $NaIO_4$ (15 mmol/L), oscillating on the oscillator at the room temperature for 30 minutes; adding 1 ml 2 mol/L ethylene glycol solution to stop oxidization, and continuing light oscillation for 30 minutes; after stopping oscillation, washing with 10 ml $Na_2CO_3$ solution (a buffer solution at pH 9.5) for three times; after washing, immediately adding a protein solution prepared by the same buffer solution, oscillating them for carrying out a binding reaction at 4° C. or room temperature for 18~20 hours (the protein concentration ranging between 10~20 mg/ml G75); centrifuging to eliminate the supernatant, adding 2 ml sodium borohydride solution (1 mg/ml, prepared by 0.01 mol/L PB), further oscillating for 1 hour; eliminating the sodium borohydride, washing with 10 ml PB for three times; and 2 ml sodium thiocyanate (3 mol/L, prepared by 0.01 mol/L pH6.0 phosphate buffer solution) for twice, and oscillating for each time for 30 minutes, finally, using 10 ml PB to wash for three times.

Using 1 g of the above prepared albumen-bound glucan cross-linked microsphere, in dry state, the ranging of particle diameter between 40 µm and 120 µm, and in hydrometric state with water content ~88%, magnetic polymer 21 was prepared according to the method of example 1, except for controlling the pH value at 12, heating to 80° C. for reacting for 30 minutes. The measured saturated magnetization strength of the magnetic polymer 21 was 27.15 emu/g.

As seen from Examples 21, for a water soluble natural polymer derivative having coordination capability, magnetic particles can be smoothly introduced through once magnetic transformation by the method of the present invention.

Example 22

A submicron human serum albumin and staphylococcal bacteria A albumen co-blend microsphere was synthetic by a method comprising: in a 20 ml round-bottom glass tube, dissolving 31.25 mg human serum albumin and 7.0 mg staphylococcal bacteria A albumen in 125 µl distilled water; adding 10 ml cotton seed oil pre-heated to 26° C.; stirring strenuously at 26° C. for 10 minutes so as to mix with cotton seed oil; cooling the mixture liquid to 4° C., ultrasonic emulsifying in the ice bath for 3 times, 1 minute for each time, with a power of 100 watt; spraying the emulsion into 100 ml cotton seed oil at 120° C., and continuously stirring for 10 minutes; washing with absolute ethyl ether by centrifuging (2600×g, 10 minutes) for 4 times.

Using 1 g of the above prepared submicron human serum albumin and staphylococcal bacteria A albumen co-blend microsphere, the microsphere having an average diameter of about 500±100 nm, in hydrometric state with water content 50~60%, magnetic polymer 22 was prepared according to the method of example 1, except for controlling the pH value at 12, heating to 80° C. for reacting for 30 minutes. The measured saturated magnetization strength of the magnetic polymer 22 was 28.63 emu/g.

As seen from Examples 22, for a mixture of a water soluble natural polymer having coordination capability and other substance, magnetic particles can be smoothly introduced through once magnetic transformation by the method of the present invention.

Example 23

Using 1 g of millimeter gelose cross-linked microsphere, Sepharose 4B produced by Pharmacia, the microsphere diameter ranging between 40 µm and 190 µm, in hydrometric state with water content ~96%, magnetic polymer 23 was prepared according to the method of example 1, except for controlling the pH value at 12, heating to 80° C. for reacting for 30 minutes. The measured saturated magnetization strength of the magnetic polymer 23 was 23.19 emu/g.

As seen from Examples 23, magnetic particles can be smoothly introduced into a physically cross-linked polymer through magnetic transformation for once by the method of the present invention.

Example 24

Using 1 g of the same micron macroporous monodisperse polyacrylic acid cross-linked microsphere as in example 8, the particle diameter being 4.73 µm, in hydrometric state with water content 140~160%, magnetic polymer 24 was prepared according to the method of example 1, except for what was added was 10 ml 0.1 mol/L $MnSO_4.H_2O$ solution. The measured saturated magnetization strength of the magnetic polymer 24 was 18.55 emu/g.

Example 25

Using 1 g of the same micron macroporous monodisperse polyacrylic acid cross-linked microsphere as in example 8, the particle diameter being 4.73 µm, in hydrometric state with water content 140-460%, magnetic polymer 25 was prepared according to the method of example 1, except for what was added was 10 ml 0.1 mol/L $CoCl_2.6H_2O$ solution. The measured saturated magnetization strength of the magnetic polymer 25 was 19.11 emu/g.

As seen from Examples 24 and 25, when using other divalent metal ions to replace $Fe^{2+}$ ion, the method as disclosed by the present invention still can smoothly introduce magnetic particles into a polymer through magnetism transformation for once.

Comparative Example 1

The comparative example 1 was carried out by using 1 g of the sane millimeter micropore type acrylic cation exchange resin 110 produced by the Chemical Plant of NanKai University as used in example 1, 1 g of millimeter macropore type acrylic cation exchange resin D151 produced by the Chemical Plant of NanKai University as used in example 2, and 1 g of millimeter macropore type sulfonic group-bound styrene cation exchange resin D72 produced by the Chemical Plant of NanKai University as used in example 3.

With reference to the method described in U.S. Pat. No. 4,774,265, 3 portions of 20 ml aqueous iron salt mixture solution containing 0.05 mol/L $(NH_4)_2Fe(SO_4)_2.6H_2O$ and 0.1 mol/L $FeCl_3.6H_2O$ were added to the above resin microspheres, stirred, and then centrifuged to decant the unabsorbed solution. Subsequently, deionize water was used for washing again by dispersing and centrifuging for 6 times, and the resultant was controlled to a pH value at 13 by adding concentrated ammonia water, heated to 80° C., and stirred for 30 minutes. The solution turned brown from white, no magnetism.

Repeating the above operation again, the solution turned red, no magnetism.

Repeating the above operation for the third time, the solution turned black, having magnetism. It was measured that the final saturated magnetization strengths of the three samples were respectively 23.07 emu/g, 31.28 emu/g, and 25.44 emu/g.

Further, similar results were obtained by changing the mol ratios of $Fe^{2+}/Fe^{3+}$ in the aqueous iron salt mixture solution to 1:1, 2:1, 5:1 and 20:1, respectively.

Comparative Example 2

The comparative example 2 was carried out by using 5 g of the same micron macroporous monodisperse polyacrylic acid cross-linked microsphere as in example 8, the particle diameter being 4.73 μm, in hydrometric state with water content 140~160%, which was divided into 5 portions, 1 g each portion.

5 portions of 20 ml $(NH_4)_2Fe(SO_4)_2 \cdot 6H_2O/FeCl_3 \cdot 6H_2O$ mixture solutions were further prepared, wherein the concentration of $FeCl_3 \cdot 6H_2O$ was fixed to 0.1 mol/L, while the concentration of $(NH_4)_2Fe(SO_4)_2 \cdot 6H_2O$ was respectively changed to 0.05 mol/L, 0.1 mol/L, 0.2 mol/L, 0.5 mol/L and 2.0 mol/L, thereby the $Fe^{2+}/Fe^{3+}$ mol ratios of the five portions of iron salt mixture solutions were respectively 1:2, 1:1, 2:1, 5:1, and 20:1.

With reference to the method of U.S. Pat. No. 4,774,265, 20 ml of aqueous iron salt mixture solution were respectively added into the polymers, stirred, and then centrifuged to decant the unabsorbed solution. Subsequently, deionize water was used for washing again by dispersing and centrifuging for 6 times, and the resultant was transferred into a flask, which was vacuumized and subsequently introduced with nitrogen gas. Concentrated ammonia water was added under the protection of nitrogen gas to control the pH value at 13, and then the resultant was heated to 80° C., stirred for 30 minutes. None of the 5 samples have magnetism in their resultants. It is still no magnetism after repeating for 3 times.

As seen from comparative examples 1-2, in the case where the method of the U.S. Pat. No. 4,774,265 was used, for the millimeter micropore type acrylic cation exchange resin 110, the millimeter macropore type acrylic cation exchange resin D151, and the millimeter macropore type sulfonic group-bound styrene cation exchange resin D72, strong magnetism can only be exhibited after three times of magnetism transformation, while for the micron macroporous monodisperse polyacrylic acid cross-linked microsphere, no magnetic polymer can be obtained by repeating magnetism transformation for three times even under a $Fe^{2+}/Fe^{3+}$ mol ratio as high as 20:1.

To sum up, the present invention provided a simple method for introducing magnetic particles into a polymer for further preparing magnetic polymer, the method using the capability of polymers to absorb $Fe^{3+}$ ions and other divalent metal ions $M^{2+}$, adding alkali immediately each time after absorbing a kind of cation, thereby generating hydrated oxide of the $Fe^{3+}$ ions and hydrated oxide of the divalent metal ions in sequence inside the polymer; upon heating, the hydrated oxide of the $Fe^{3+}$ ions and the hydrated oxide of the divalent metal ions were transformed into magnetic particles. The advantages of the method lie in: simple in procedures, for it needs no consideration of the $M^{2+}/Fe^{3+}$ proportion, needs no continuously adjusting the formula of the iron salt mixture relative to different polymers, needs no consideration of shapes of the polymers, because it is applicable for both regular shaped polymers and irregular shaped polymers; not only suitable for large particle diameter polymers, but also suitable for polymers of micro or smaller sizes.

The invention claimed is:

1. A method for preparing a magnetic polymer, comprising:
   a) putting a polymer in a container, the polymer having groups capable of absorbing $Fe^{3+}$ ions and $Fe^{2+}$ ions or other divalent metal ions, and having large pores within the molecule or being capable of forming a microporous gel in a solution;
   b) adding a $Fe^{3+}$ salt solution into the polymer of a), and stirring to make the polymer absorb $Fe^{3+}$ ions;
   c) washing the resultant polymer of b) to eliminate unabsorbed $Fe^{3+}$ ions, adding an alkaline solution to control the pH value in a range from 9 to 14, stirring, and then washing to neutral;
   d) adding a divalent metal salt solution into the polymer of c), and stirring to make the polymer absorb divalent metal ions;
   e) washing the resultant polymer of d) to eliminate the unabsorbed divalent metal ions; and
   f) introducing an inert gas, adding an alkaline solution to control the pH value in a range from 9 to 14, stirring and heating for a period of time sufficient to produce a magnetic polymer, wherein a method for preparing a magnetic polymer is afforded.

2. The method according to claim 1, wherein said polymer comprises a water soluble cross-linked polymer.

3. The method according to claim 1, wherein said polymer comprises a water soluble natural polymer and derivatives thereof.

4. The method according to claim 3, wherein said water soluble natural polymer and derivatives thereof include at least one selected from the group consisting of pectin, heparin, animal serum albumin, gelose, glucan and their derivatives.

5. The method according to claim 1, wherein said polymer comprises a synthetic polymer having cation exchange capability.

6. The method according to claim 5, wherein said synthetic polymer having cation exchange capability comprises one formed by homopolymerization or copolymerization of monomer(s) having at least one group selected from the group consisting of —$SO_3H$, —COOH, —$PO_3H_2$, —CONH—OH in the molecule, or one introduced with the above groups by chemical modification.

7. The method according to claim 1, wherein said polymer is a synthetic polymer having single coordination or chelating capability.

8. The method according to claim 7, wherein said synthetic polymer having single coordination or chelating capability comprises at least one selected from the group consisting of polyacrylamide, polyvinyl alcohols, polyvinyl pyridine, and polyvinyl amine, or imine carboxylic acids having both amino group and carboxyl group in a molecule, phosphoramidic acid structure, and proline structure.

9. The method according to claim 1, wherein the $Fe^{3+}$ salt includes $FeCl_3$ and its hydrates, $Fe(NO_3)_3$ and its hydrates, $(NH_4)Fe(SO_4)_2$ and its hydrates, $(NH_4)_3[Fe(C_2O_4)_3]$ and its hydrates, $Fe(ClO_4)_3 \cdot xH_2O$, ferric citrate, and ferric ammonium citrate.

10. The method according to claim 1, wherein said divalent metal salt comprises a divalent metal compound capable of forming magnetic $MFe_xO_y$ particles with $Fe^{3+}$ ions, where M includes $Fe^{2+}$, $Zn^{2+}$, $Mg^{2+}$, $Cu^{2+}$, $Ca^{2+}$, $Ba^{2+}$, $Sr^{2+}$, $Ni^{2+}$, $Co^{2+}$, $Mn^{2+}$; x=1.0~2.0; and y=3.0~4.0.

* * * * *